United States Patent [19]

Spitzner

[11] 4,294,961

[45] Oct. 13, 1981

[54] BENZOTHIAZINE 1,1-DIOXIDES

[75] Inventor: Ernest Spitzner, Minneapolis, Minn.

[73] Assignee: Henkel Corporation, Minneapolis, Minn.

[21] Appl. No.: 137,869

[22] Filed: Apr. 7, 1980

[51] Int. Cl.[3] ............................................ C07D 279/02
[52] U.S. Cl. ..................................................... 544/49
[58] Field of Search ......................................... 544/49

[56] References Cited

U.S. PATENT DOCUMENTS 3,284,450 11/1966 Kraaijeveld et al. ................. 544/49
3,346,572 10/1967 Shavel et al. ......................... 544/49
3,966,716 6/1976 Kaminsky ............................. 544/49

FOREIGN PATENT DOCUMENTS 2124953 12/1971 Fed. Rep. of Germany .

OTHER PUBLICATIONS

J. von Braun, Chem. Ber., vol. 56, pp. 2332–2343 (1923).
Abe, J. Pharm. Soc., Japan, vol. 76, pp. 1058–1063 (1956).
Abe, Chem. Abstracts, vol. 51, entry 3499e (1957).
Zinnes et al., J. Org. Chem., vol. 30, pp. 2241–2246 (1965).
Rasmussen, J. Org. Chem., vol. 39, pp. 1554–1560 (1974).
Abed, Jour. Indian Jour. of Chem., vol. 14B, pp. 428–429 (1976).
M. von Strandtmann et al., J. Hetero. Chem., vol. 9, pp. 171–172 (1972).
Lombardino et al., Jour. of Medicinal Chemistry, vol. 14, pp. 1171–1175 (1971).

*Primary Examiner*—John M. Ford

*Attorney, Agent, or Firm*—Patrick J. Span

[57] ABSTRACT

Certain benzothiazine compounds, metal complexes thereof and solutions of said compounds in essentially water-immiscible, liquid hydrocarbon solvents are disclosed. These compounds have in their 4-keto form, the structure:

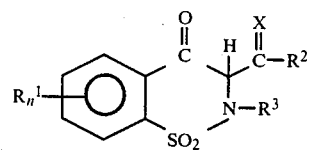

the corresponding enol of which has the structure:

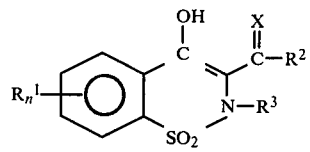

wherein x, n, $R^1$, $R^2$ and $R^3$ are as defined in the specification and claims hereof. Particular metal values are recovered from their aqueous solutions by using the benzothiazine compounds dissolved in essentially water-immiscible, liquid hydrocarbon solvents. The extraction process involves contacting the metal value containing aqueous solution with the solution of the benzothiazine in essentially water-immiscible, liquid hydrocarbon solvent and stripping the metal from the loaded organic phase.

16 Claims, No Drawings

BENZOTHIAZINE 1,1-DIOXIDES

The present invention is directed to novel benzothiazines, organic solvent solutions thereof, metal complexes of the benzothiazines and organic solutions of such complexes, and the method of using said benzothiazines to extract metal values from aqueous solutions.

Liquid ion exchange recovery of metal values from aqueous solutions thereof has in the past ten years or so become a mature commercial operation. Such processing has been described as being deceptively simple since all that is really happening is the transfer of a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities, and (3) engineering application leading to large scale metal recovery.

The key to a successful application of liquid ion exchange is the reagent. In this respect, the reagent should desirably meet a number of criteria. In the first instance, the reagent should complex with or react with a metal or group of metals and such complexing or reaction should be relatively fast in order to avoid having to use large holding tanks or reaction vessels. It is also desirable that the reagent exhibits preference for a single metal where the aqueous starting solutions contain a number of metal values. Such selectivity can often be optimized at designated pH ranges. The reagent should also desirably complex or react quantitatively with the metal under the extraction conditions. Additionally, the reagent, as well as the resulting metal complex, must exhibit satisfactory solubility in the essentially water-immiscible organic solvent being used. Further, the reagent-metal reaction or complexing should be reversible so that the metal can be stripped from the organic phase. For economic reasons, the reagent should be relatively stable so that it can be recycled repeatedly. Also, it should be essentially water insoluble to prevent significant loss into the aqueous phase or phases. Furthermore, the reagent should not cause or stabilize emulsions. Again and principally for economic reasons, the reagent should not react with or load significant quantities of acid, for example, from aqueous acidic stripping solutions. And, of course, the cost of the reagent should be such that the liquid ion exchange process can be operated at a profit.

Of significant, but lesser, importance, is the selection of the essentially water-immiscible solvent to be used in the liquid ion exchange process. Such selection is important principally from a cost standpoint, especially in the recovery of the more common metals. Existing commercial operations for copper recovery, for example, generally employ aliphatic kerosenes because of the low cost thereof. Thus, the cost of the reagent and the solvent is intertwined in providing the desired overall economics of the process being commercialized.

One of the most extensively used systems in commercial operation in the last decade for copper recovery has employed benzophenoximes or combination reagents including a benzophenoxime component. Other types of reagents which have been proposed for use in copper recovery are the alkenyl substituted 8-hydroxyquinolines. Among other more recent reagents are the sulfonamido oximes of U.S. Pat. No. 4,160,807 and sulfonamidoquinolines of U.S. Pat. No. 4,100,163.

It has now been discovered that certain benzothiazines, as more fully defined hereinafter, are useful in liquid ion exchange recovery processes. The benzothiazines useful in the present invention are represented by the following general structural formula (represented in the 4-keto form):

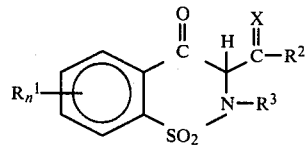

the corresponding enol of which has the structure:

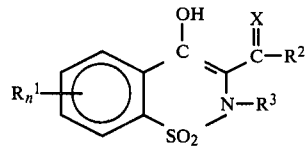

wherein
X represents oxo or oxime;
$R^1$ and $R^3$ may be hydrogen or an alkyl, alkenyl, aralkyl, alkaryl or alkenylaryl radical containing from 1 to about 20 carbon atoms;
n represents zero or an integer ranging from 1 to 4;
$R^2$ represents a radical which can be alkyl, alkenyl, alkaryl or alkenylaryl containing from 1 to 20 carbon atoms; and provided that at least one of $R^2$ and $R^3$ contains at least 8 carbon atoms.

Accordingly when $R^3$ is hydrogen, $R^2$ must contain at least 8 carbon atoms. Thus it is preferred that the compounds contain at least one alkyl group having at least 8 carbon atoms. Additionally the alkyl and alkenyl groups may be substituted or unsubstituted, linear or branched chain, although the branched chain is preferred. Because the utility of the compounds of the present invention resides in their ability to form organic solutions which are capable of extracting metal values from aqueous solutions, various substituents which do not interfere with chelation or stability may be appended to the alkyl, alkenyl or aryl substituents without departing from the scope of the invention. Illustrative of such groups are electron withdrawing groups such as halogen (i.e., Cl, Br) ester, ether, nitrile, nitro, and the like.

The compounds of the present invention are also characterized as having solubilities in essentially water-immiscible liquid hydrocarbon solvents of at least 2% by weight. Correspondingly, they are further characterized in that the copper ($Cu++$) complexes of the compounds have solubilities of at least 2% by weight in the said water-immiscible liquid hydrocarbon solvents. Especially preferred compounds of the invention are those which exhibit solubilities of at least 2% by weight in both pure and complexed form, in aliphatic or aromatic hydrocarbons, or mixtures thereof, having flash points of at least 150° F. Thus, the compounds of the invention may preferably be further characterized as having substituents containing a sufficient number of carbon atoms and/or branching in the alkyl chains to provide at least the minimum 2% solubility in the aforementioned solvents.

The preference for alkyl substituents containing at least 8 carbon atoms and/or possessing a branched chain structure is due to their contribution to the solubilities of the compounds in the above described solvents. The beneficial effect provided by the number of carbon atoms is obtained by having an alkyl substituent of at least 8 carbon atoms. Accordingly, the most preferred compounds of the present invention are those possessing one or more branched chain alkyl substituents having at least 8 carbon atoms.

The classical synthesis route for the 3-acyl-2H-1,2-benzothiazin-4(3H)one-1,1-dioxides is practical for use in this invention, since the desired 1,2-benzothiazine-1,1-dioxide nucleus can be obtained from readily available starting materials such as the alkali metal saccharins, sodium and potassium saccharin being most commonly mentioned in the literature. The first step of the classical synthesis of J. von Braun, Ber., 56:2332(1923) or Abe et al, *J Pharm. Soc. Japan*, 76:1058(1956) abstracted in *Chem. Abs.* 51:3499e(1957) involves reaction of the sodium or potassium saccharin with the compound $R^2CO$—$CH_2Cl$, wherein $R^2$ is as defined previously. In those cases wherein compounds of the formula $R^2CO$—$CH_2Cl$ (or an equivalent halide) are not readily available, these starting materials can be synthesized from a suitable alpha-halo acid halide and the desired hydrocarbon which will provide the desired $R^2$ radical. The reaction is carried out in the presence of aluminum chloride, as follows:

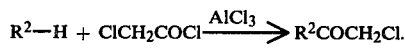

for example, p-dodecylphenacyl chloride can be prepared in this manner from dodecylbenzene and chloroacetyl chloride, both the alkylbenzene and the chlorinated acid chloride being commercially available.

Upon completion of this first step, the product which has been obtained can be represented by the structural formula

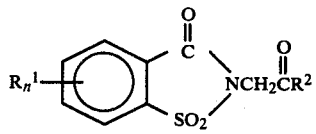

wherein $R^1$, n, and $R^2$ are as defined previously.

The next step in the synthesis involves rearrangement of the five-membered heterocycle of the above-described structure. Strong basic conditions provided by an ethanolic solution of sodium methoxide or the like provides the 3-acyl-2H-1,2-benzothiazin-4(3H)one-1,1-dioxide in good yield, typically ranging from at least 60% to slightly less than 100%. To obtain N-substitution of the 1,2-thiazine portion of the compound and/or to convert the exocyclic carbonyl (i.e., the acyl carbonyl) to an oxime, further steps are carried out in a manner generally known in the art. The amido nitrogen at the 2-position of the fused, 1,2-thiazine ring can be converted to, for example, N-aliphatic by reaction with the monochlorinated aliphatic compound in the presence of a hydride and a suitable solvent such as dimethyl sulfoxide. Such a reaction can be represented as follows:

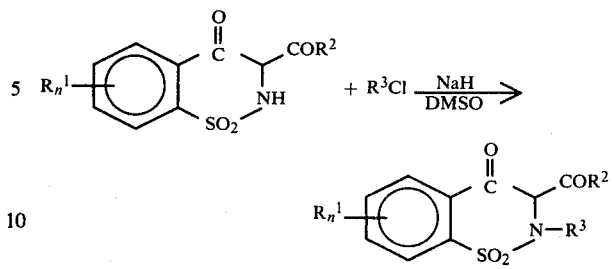

wherein $R^1$, n, $R^2$, and $R^3$ are as defined previously.

The conversion of the exocyclic carbonyl to an oxime is carried out in the usual manner with hydroxylamine or its hydrochloride. One preferred technique is to react this carbonyl with hydroxylamine-hydrochloride in sodium acetate/methanol, whereby the —$COR^2$ becomes

Although the 3-acyl-2H-1,2-benzothiazin-4(3H)one-1,1-dioxides have been known at least since the early work of Abe et al (reported in 1956), it has been only relatively recently that investigation of the commercial potential of this class of benzothiazine-1,1-dioxide compounds has begun in earnest, generally in respect to pharmaceutical utility and biological activity. Reference may be made to Zinnes et al, *J Org. Chem.*, 30:2241 (1965); C. R. Rasmussen, *J. Org. Chem.*, 39:1554 (1974); M. M. Abed, *Indian Journal of Chemistry*, 14B:428 (1976; Vonstandmann et al, *J Heterocycl. Chem.*, 9:171 (1972); Lombardino et al, *J Mednl. Chem.*, 14:1171 (1971); and in the patent literature to Shavel et al, U.S. Pat. No. 3,346,572, issued Oct. 10, 1967; Kraaijeveld et al, U.S. Pat. No. 3,284,450, issued Nov. 8, 1966; and West German Offenlegungsschrift No. 2,124,953 (December, 1971).

As indicated, my new benzothiazine compounds find use in the recovery of metal values from their aqueous solutions. In said process, the compounds are dissolved in an essentially water-immiscible organic solvent and then the resulting solution is contacted with the metal containing aqueous phase to extract at least a portion of the metal values into the organic phase. The phases are separated and metal values are stripped from the loaded organic phase by the use of an aqueous stripping medium.

A wide variety of essentially water-immiscible, liquid hydrocarbon solvents can be used in the metal recovery process of the present invention. These include: aliphatic and aromatic hydrocarbons such as kerosenes, benzene, toluene, xylene and the like. The choice of the said essentially water-immiscible liquid hydrocarbon solvent for particular commercial operations will depend on a number of factors including the design of the solvent extraction plant (i.e., mixer-settlers, Podbielniak extractors, etc.), the value of the metal being recovered, disposal of plant effluent and the like. The process of the present invention finds particular use in the extraction recovery of the major, non-ferrous, transition metals—i.e., copper, nickel, zinc, cobalt (II) and cobalt (III), as will be described more fully hereinbelow. Essentially, all of the major plants in operation currently for the recovery of these metals (particularly Cu++) use mixer-settlers with relatively large organic inventories and some loss of solvent invariably occurs by evaporation, entrainment in the aqueous, and the like. Under these circumstances, preferred solvents for use in the metal recovery processes of the present invention are the aliphatic and aromatic hydrocarbons having flash points of 150° F. and higher and solubilities in water of less than 0.1% by weight. These solvents are also essentially non-toxic and chemically inert and the costs thereof are currently within practical ranges.

Representative commercially available solvents are Kermac 470B (an aliphatic kerosene available from Kerr-McGee—Flash Point 175° F.), Chevron Ion Exchange Solvent (available from Standard Oil of California—Flash Point 195° F.), Escaid 100 and 110 (available from Exxon-Europe—Flash Point $\approx$ 180° F.), Norpar 12 (available from Exxon-U.S.A.—Flash Point 160° F.), Conoco C-1214 (available from Conoco—Flash Point 160° F.), Aromatic 150 (an aromatic kerosene available from Exxon-U.S.A.—Flash Point 150° F.) and various other kerosenes and petroleum fractions available from other oil companies.

The present invention thus additionally relates to new compositions wherein the benzothiazine compounds of the invention are dissolved in the essentially water-immiscible, liquid hydrocarbon solvents described above. In this regard, liquid ion exchange reagents are often sold as solutions in organic solvents. These new compositions consist essentially of solutions of at least 2% by weight of the benzothiazine in essentially water-immiscible, liquid hydrocarbon solvents. When sold as concentrates, the solutions will preferably contain from about 25 to 75% by weight of the benzothiazine.

In the process of the present invention, the organic solvent solutions will preferably contain from about 2 to 75% by weight of the benzothiazine compounds and even more preferably from about 5 to 20% by weight thereof. Additionally, volume ratios of the organic-:aqueous phase vary widely since the contacting of any quantity of the benzothiazine solution with the metal containing aqueous phase will result in extraction of metal values into the organic phase. However, for commercial practicality the organic:aqueous phase ratios are preferably in the range of about 5:1 to 1:5. For practical purposes, the extracting and stripping are normally conducted at ambient temperatures and pressures although higher or lower temperatures and/or pressures are entirely operable. Most advantageously, the entire process can be carried out continuously with the stripped organic solvent solution being recycled for contacting further quantities of metal containing solutions.

The present invention also relates to the metal complexes of the novel benzothiazine compounds and to the essentially water-immiscible, liquid hydrocarbon solvent solutions thereof. The solutions consist essentially of the said solvent and at least 2% by weight, and preferably less than 75% by weight, of the metal complexes. While not normally practiced in the industry, the solutions of the metal complexes can be obtained at one location and transported to another for stripping as hereinafter described. The term "metal complex" as used herein is meant to connote compositions of the novel benzothiazine with other than insignificant quantities of metal ions. Although the exact structural nature of these complexes has not been ascertained, tests have indicated that under conditions of maximum loading, particularly with $Cu^{++}$ and $Zn^{++}$ metal ions, the complexes comprise the metal and benzothiazine compound in a molar ratio of 1:2. Maximum loading, however, is not required for achieving acceptable performance in liquid ion exchange processes and hence the metal complexes are generally defined as including the designated metals in more than insignificant quantities up to maximum loading.

The metal recovery process of the present invention is useful for the recovery of the following metal values from their aqueous solutions: $Cu^{++}$, $Ni^{++}$, $Zn^{++}$, $Co^{++}$, and $Co^{+++}$. These metal values are all transition metals of Groups Ib, IIb and VIII. The extraction of these various metal from aqueous solutions depends upon a number of factors including, for example, the concentration of the metal ion, the particular anions present, and the pH of and/or ammonia concentration in the aqueous solutions, as well as the particular benzothiazine chosen and its concentration in the organic phase. Generally, it is preferred to extract the metal values from ammoniacal solutions in which the preferred concentration of ammonia is from about 10 to 150 g/l. However, it is understood that for each aqueous metal solution and benzothiazine reagent solution there will be a preferred or optimum set of extraction conditions, and those skilled in the art, based on the information given herein, especially in the examples to follow, will be able, after a limited number of trial runs, to determine such preferred or optimum conditions for the respective systems under consideration. This is equally true of the stripping operations. By the term stripping is meant the transfer of at least a portion of the metal values in the loaded organic phase to the aqueous stripping medium. The metal values so stripped are desirably recovered from the aqueous stripping medium by conventional techniques, preferably electrolysis. The volume ratios of loaded organic:aqueous stripping phase can also vary widely. However, the overall object of the process is to provide a metal containing stripping solution of known composition and concentration suitable for conventional recovery techniques such as electrolysis. Accordingly, the metal will preferably be present in higher concentrations in the aqueous stripping medium than in the starting metal containing solution. To accomplish this, the loaded organic:aqueous stripping medium phase ratio will normally be in the range of about 1:1 to 10:1. The stripping medium is preferably an aqueous mineral acid solution such as 25 to 250 g/l $H_2SO_4$.

While the process of the present invention has been described as particularly effective in extracting $Cu^{++}$, $Ni^{++}$, $Zn^{++}$, $Co^{++}$ and $Co^{+++}$, metal values from aqueous solutions, it may be applied, with less effectiveness, to extract other chemically similar metal values.

The process of the invention thus provides a simple, continuous method of extracting valuable metal values from aqueous solutions. Of equal importance is the economic advantages attendant from the process which allows the extracting reagent to be stripped of metal values and recycled for subsequent loading.

To further illustrate the various objects and advantages of the present invention, the following examples are provided. It is understood that their purpose is entirely illustrative and in no way intended to limit the scope of the invention.

EXAMPLE 1

Preparation of Starting Materials

A. p-Dodecylphenacyl chloride

In accordance with the procedure in Org. Syn., Coll. Vol. 3, page 183, carbon disulfide (225 ml) chloroacetyl chloride (0.35 mole) and dodecylbenzene (0.2 mole) were placed in a 1-liter, 3-neck flask fitted with a mechanical stirrer, 2 condensers in series with a drying tube and a 125-ml. flask (containing aluminum chloride) attached by tubing. Six tenths of a mole (80 g) of aluminum chloride was added portionwise, with vigorous stirring, over a half-hour period. After the addition of $AlCl_3$ was completed, the reaction mixture was refluxed for 45 minutes and permitted to stand overnight. After the overnight period, the remaining $AlCl_3$ was decomposed with hydrochloric acid and the product was worked up in a organic phase ("Skelly B"), separated, washed, dried, and isolated as a dark green oil. Nuclear magnetic resonance (NMR) and infrared (IR) confirmed the product as p-dodecylphenacyl chloride.

B. N-Acetonylsaccharin and its p-dodecylphenacyl analog

In accordance with Eckenroth et al, Ber. 29:329 (1896), sodium saccharin (the sodium salt of 1,2-benzisothiazol-3(2H)-one 1,1-dioxide) was combined with $R^2COCH_2Cl$ with heating on a steam bath and occasional agitation at least an hour and then allowed to stand overnight. The reaction mixture is then chilled with cold water, filtered, and recrystallized from solvent or worked up in an organic solvent to a gummy residue, depending upon the nature of the product. When $R^2$ was methyl, $R^2COCH_2Cl$ was chloroacetone, a liquid which served as part of the liquid reaction medium, hence the molar ratio of chloroacetone to sodium saccharin was 2.7:1. Heating on the steam bath was maintained for 6 hours, and a crystalline product was obtained by crystallization from hot ethanol. When $R^2$ was p-dodecylphenyl, $R^2COCH_2Cl$ was the starting material of Section A of this Example. Heating to 60° C. was maintained for 2 hours, and the gummy precipitate obtained after cooling of the reaction mixture was worked up in ether, washed, and dried, filtered and evaporated under vacuum to an orange, viscous liquid.

C. 3-Acetyl-2H-1,2-benzothiazin-4(3H)one-1,1-dioxide

The N-acetonylsaccharin of Section B of this Example was treated with sodium methoxide in accordance with Zinnes et al, J. Org. Chem., 30:2241 (1965), U.S. Pat. No. 3,284,450, and Rasmussen, J. Org. Chem., 39:1554 (1974). Laboratory reagent sodium methoxide (0.9 mole) was blended with 50 ml of absolute ethanol and heated to 40° C.; 0.04 mole of the N-acetonylsaccharin was then added and the resulting mixture heated with stirring to 60° C. The mixture was then cooled and acidified with 5% HCl, resulting in the formation of a precipitate. The precipitate was washed, dried, filtered and evaporated to give an oily solid in 68% yield.

EXAMPLE 2

3-(p-Dodecylbenzoyl)-2H-1,2-benzothiazin-4(3H)one 1,1-dioxide

The procedure of Example 1(C) was followed to convert the p-dodecylphenyl analog of N-acetonylsaccharin (see Example 1[B]) to the desired 3-acyl-1,2-benzothiazin-4(3H) one-1,1-dioxide. The product was obtained in 98% yield.

EXAMPLE 3

2-Dodecenyl-3-acetyl-2H-1,2-benzothiazin-4(3H)one 1,1-dioxide

Fifteen millimoles of the product of Example 1(C) were reacted with 20 millimoles of dodecenyl chloride in the presence of 15 millimoles of NaH and 25 ml of dimethylsulfoxide in accordance with Zinnes et al, J. Org. Chem., 30:2241 (1965). The product of Example 1(C) was dissolved in the dimethylsulfoxide (DMSO) and the sodium hydride was added to the resulting solution, followed by addition of the n-dodecenyl chloride. A precipitate formed, accompanied by an exotherm. The reaction mixture was then heated to a temperature within the range of 75° to 80° C. for 30 minutes, resulting in solution of the precipitate. The mixture was then cooled, acidified, and the product extracted with ether, washed, dried and purified with solvents to provide a 79% yield of an orange liquid product.

EXAMPLE 4

2-Dodecenyl-3-acetyl-2H-1,2-benziothiazin-4(3H) one 1,1-dioxide, oxime

The product of Example 3 (15 millimoles) was converted to the corresponding oxime by reacting the exocyclic (3-acyl) carbonyl with hydroxylamine hydrochloride (18 millimoles) in the presence of sodium acetate (20 millimoles) and absolute methanol (20 ml). The aforementioned ingredients were combined and refluxed overnight. The resulting mixture was cooled, and the product was extracted with ether, washed, dried, filtered and evaporated to give a cloudy orange oil in 84% yield.

EXAMPLE 5

Extraction of Metal Values

To determine the ability of selected compounds of the present invention to extract metal values from aqueous solutions, tests were conducted in accordance with the following procedure:

A 0.1 M solution of the compounds of Examples 2, 3 and 4 above in "SOLVESSO 150" (trademark for aromatic kerosene having a flash point of 150° F.) and five aqueous solutions of the following compositions were used:

| Metal | Composition |
| --- | --- |
| $Cu++$ | 0.05 M $CuSO_4$ (3.2 g/l $Cu++$), 0.4 M $NH_3$, and 0.1 M $(NH_4)_2SO_4$ |
| $Ni++$ | 0.05 M $NiSO_4$ (2.9 g/l $Ni++$), 0.4 M $NH_3$, and 0.1 M $(NH_4)_2SO_4$ |
| $Zn++$ | 0.05 M $ZnSO_4$ (3.2 g/l $Zn++$), 0.4 M $NH_3$ and 0.1 M $(NH_4)_2SO_4$ |
| $Co++$ | 0.025 M $CoSO_4$ (1.5 g/l $Co++$), 1.7 M $NH_3$ and 0.1 M $(NH_4)_2SO_4$ prepared as needed under an atmosphere of nitrogen |
| $Co+++$ | 0.025 M $CoSO_4$ (1.5 gal/l $Co++$), 1.7 M $NH_3$ and 0.1 M $(NH_4)_2CO_3$ (air oxidized to $Co+++$) |

Portions of the organic solutions were shaken with the five aqueous solutions at an organic:aqueous phase volume ratio of 1:1 for one hour at ambient temperature. The organic phases were then analyzed for metal content. If a third phase was present, both the organic and aqueous phases were clarified and analyzed. Table 1 summarizes the data obtained from the extraction tests for various reagents of the present invention.

TABLE 1

| Reagent Example | Cu | Ni | Zn | Co(II) | Co(III) |
|---|---|---|---|---|---|
| 2 | 1.13* | 2.22* | 2.10* | 1.22* | 0.95* |
| 3 | 1.16 | 1.03 | .910 | .920 | .0245 |
| 4 | 1.20 | .800 | .885 | 1.14 | .0600 |

*Emulsion - metal concentration (M[org]) determined by difference.

EXAMPLE 6

Ammonia Isotherms

To determine the extent of extraction of various metal ions as a function of total ammonia concentration in the aqueous phase, tests were conducted in accordance with the following procedure:

Portions of a 0.1 molar solution of the compound of Example 2 in SOLVESSO 150 solvent were shaken at 1:1 organic:aqueous phase volume ratio for approximately one hour at ambient temperature with aqueous ammoniacal solutions containing a particular metal ion, nickel or zinc. The organic phase was then separated and analyzed for metal concentration, generating the data contained in Table 2 which demonstrates the degree of metal extraction as a function of ammonia concentration for the particular reagent system. In the tables all concentrations are given in grams per liter.

TABLE 2

| Total NH₃ | Ni Aqueous Feed | Ni [Org.] | % Extraction | Total NH₃ | Zn Aqueous Feed | Zn [org.] | % Extraction |
|---|---|---|---|---|---|---|---|
| 15.1 | .347 | .340* | 98.0 | 14.4 | .330 | .330* | 100 |
| 30.0 | .357 | .352* | 98.6 | 28.9 | .332 | .169 | 50.9 |
| 60.0 | .359 | .252 | 70.2 | 58.3 | .332 | .067 | 20.2 |
| 89.5 | .369 | .167 | 45.3 | 87.2 | .332 | .034 | 10.2 |
| 118.6 | .378 | .067 | 17.7 | 116.2 | .331 | .010 | 3.0 |
| 149.6 | .374 | .033 | 8.8 | 147.0 | .331 | .016 | 4.8 |

*Emulsion - M[org.] determined by difference

What is claimed is:

1. Benzothiazine-1,1-dioxide compounds having in their 4-keto form, the structure

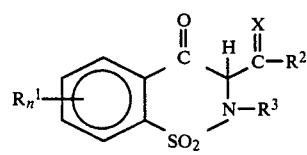

the corresponding enol of which has the structure:

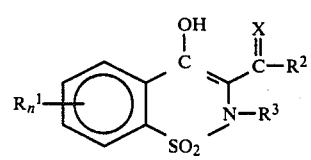

wherein
X represents a radical selected from the group consisting of oxo and oxime;
$R^1$ and $R^3$ are hydrogen or an alkyl, alkenyl, aralkyl, alkaryl or alkenylaryl radical containing from 1 to about 20 carbon atoms;
n represents zero or an integer from 1 to 4;
$R^2$ is an alkyl, alkenyl, alkaryl or alkenylaryl radical containing from 1 to about 20 carbon atoms,
and provided that at least one of $R^2$ and $R^3$ contain at least 8 carbon atoms, said compounds being further characterized as having solubilities of at least 2% by weight in essentially water-immiscible liquid hydrocarbon solvents.

2. The compounds of claim 1, wherein said liquid hydrocarbon solvent is selected from the group consisting of aliphatic and aromatic hydrocarbons and mixtures thereof having flash points of at least 150° F. and further characterized in that the Cu++ complexes thereof also have solubilities of at least 2% by weight in said liquid hydrocarbon solvents.

3. A compound according to claim 1, wherein X is oxime.

4. A compound according to claim 1, wherein X is oxo.

5. A compound according to claim 1 wherein X is oxo and n is zero.

6. A compound according to claim 1 wherein X is oxime and n is zero.

7. A compound according to claim 1 wherein n is zero, $R^2$ is methyl or p-dodecylphenyl, and $R^3$ is dodecenyl or hydrogen.

8. The compound 2-dodecenyl-3-acetyl-2H-1,2-benzothiazin-4(3H)one 1,1-dioxide.

9. The oxime of the compound of claim 8.

10. The compound 3-(4'-dodecylbenzoyl)-2H-1,2-benzothiazin-4(3H)one 1,1-dioxide.

11. A composition comprising a solution of the benzothiazine compound of claim 1 in a substantially water-immiscible, liquid hydrocarbon solvent said solution containing of at least 2% by weight of said benzothiazine compound.

12. A composition according to claim 11, wherein said solvent is selected from the group consisting of aliphatic and aromatic hydrocarbons and mixtures thereof having flash points of at least 150° F. and further characterized in that the Cu++ complexes of the benzothiazines have a solubility in said solvent of at least 2% by weight.

13. The composition of claim 11 wherein said solvent is selected from the group consisting of aliphatic and aromatic kerosenes, benzene, toluene and xylene.

14. The composition of claim 11 wherein said sulfonylhydrazone is present in an amount of about 2 to 75% by weight.

15. A composition according to claim 11 wherein n is zero, $R^2$ is methyl or p-dodecylphenyl, and $R^3$ is dodecenyl or hydrogen.

16. The composition of claim 11 wherein said benzothiazine compound is selected from the group consisting of 2-dodecenyl-3-acetyl-2H-1,2-benzothiazin-4(3H)one 1,1-dioxide,3-(4'-dodecylbenzoyl)-2H-1,2-benzothiazin-4(3H)one 1,1-dioxide, and the oximes thereof.

* * * * *